United States Patent

Kajikawa et al.

[11] Patent Number: 5,807,361
[45] Date of Patent: Sep. 15, 1998

[54] BLOOD-ABSORBENT RESIN COMPOSITION AND ABSORBENT ARTICLES

[75] Inventors: Katsuhiro Kajikawa; Takumi Hatsuda; Masatoshi Nakamura, all of Hyogo, Japan

[73] Assignee: Nippon Shokubai Co., Ltd., Osaka, Japan

[21] Appl. No.: 732,468

[22] PCT Filed: Mar. 8, 1996

[86] PCT No.: PCT/JP96/00576

§ 371 Date: Oct. 29, 1996

§ 102(e) Date: Oct. 29, 1996

[87] PCT Pub. No.: WO96/28515

PCT Pub. Date: Sep. 19, 1996

[30] Foreign Application Priority Data

Mar. 9, 1995 [JP] Japan .................................. 7-049972

[51] Int. Cl.$^6$ .................................. A61F 13/16; C08J 9/28
[52] U.S. Cl. ............................. 604/358; 521/64; 521/149; 604/369
[58] Field of Search ..................... 604/358, 369; 521/64, 149

[56] References Cited

U.S. PATENT DOCUMENTS

| H1639 | 3/1997 | Crainic | 604/368 |
|---|---|---|---|
| 4,578,068 | 3/1986 | Kramer et al. | 604/368 |
| 4,610,678 | 9/1986 | Weisman et al. | 604/368 |
| 4,666,975 | 5/1987 | Yamasaki et al. | 524/733 |
| 4,673,402 | 6/1987 | Weisman et al. | 604/368 |
| 4,693,713 | 9/1987 | Chmelir et al. | 604/368 |
| 4,734,478 | 3/1988 | Tsubakimoto et al. | 527/300 |
| 4,765,780 | 8/1988 | Angstadt | 406/123 |
| 5,047,023 | 9/1991 | Berg | 604/368 |
| 5,140,076 | 8/1992 | Hatsuda et al. | 525/375 |
| 5,156,902 | 10/1992 | Pieper et al. | 428/206 |
| 5,164,459 | 11/1992 | Kimura et al. | 525/384 |
| 5,532,350 | 7/1996 | Cottrell et al. | 536/76 |
| 5,607,414 | 4/1997 | Richards et al. | 604/378 |

FOREIGN PATENT DOCUMENTS

| 0 001 706 | 10/1978 | European Pat. Off. . |
|---|---|---|
| 0 427 316 A2 | 10/1990 | European Pat. Off. . |
| 0 429 112 A2 | 10/1990 | European Pat. Off. . |
| 54-70694 | 6/1979 | Japan . |
| 58-501107 | 7/1983 | Japan . |
| 6-207358 | 7/1994 | Japan . |
| 6-58931 | 8/1994 | Japan . |
| 6-58952 | 8/1994 | Japan . |
| 6-59039 | 8/1994 | Japan . |

*Primary Examiner*—Morton Foelak
*Attorney, Agent, or Firm*—Burns, Doane, Swecker & Mathis, LLP

[57] ABSTRACT

A blood-absorbable resin composition characterized by having a blood area ratio relative to sheep blood of not less than 30% at a basis weight of 150 g/m$^2$ and an absorbent article containing the composition. The blood-absorbable resin composition of this invention possesses an excellent ability to absorb blood and, therefore, is highly useful for sanitary napkins, tampons, medical blood-absorbable articles, trauma protectors, trauma healing materials, and reagents for treating liquid refuses from surgical operations.

11 Claims, No Drawings

BLOOD-ABSORBENT RESIN COMPOSITION AND ABSORBENT ARTICLES

TECHNICAL FIELD

The present invention relates to a resin composition which excels in the property of absorbing blood. More particularly, this invention relates to a blood-absorbable resin composition which is appropriately applied for sanitary napkins, tampons, medical blood-absorbable articles, trauma protectors, trauma healing materials, and reagents for treating liquid refuses from surgical operations.

BACKGROUND ART

In recent years, the absorbent resin has been finding extensive utility as one of the components for such sanitary materials as disposable diapers and sanitary napkins which are used for the purpose of absorbing body liquids.

As such absorbent resins, partially neutralized cross-linked polyacrylic acids (JP-A-55-84,304, JP-A-55-108, 407, JP-A-55-133,413), hydrolyzed starch-acrylonitrile graft polymer (JP-A-46-43,995), neutralized starch-acrylic acid graft polymer (JP-A-51-125,468), saponified vinyl acetate-acrylic ester copolymers (JP-A-52-14,689), hydrolyzed acrylonitrile copolymers or acrylamide copolymers (JP-53-15,959) or products of cross-linkage thereof, and cross-linked cationic monomers (JP-A-58-154,709 and JP-A-58-154,710) have been known to the art, for example.

As the characteristics which the absorbent resins are expected to possess, high ratio of absorption capacity and high speed of absorption, excels in permeability to liquid, strength of the swelled gel, and large suction power of water from the substrate wet with an aqueous liquid may be cited, for example. These characteristics, however, do not invariably show positive correlation. For example, such physical properties as permeability to liquid, gel strength, and speed of absorption are lowered in proportion as the ratio of absorption capacity is heightened. As a means to improve the absorption characteristics of the absorbent resin in fine balance, the technique of cross-linking the neighborhood of surface of the absorption resin has been known. Various methods have been proposed to date concerning this technique. For example, methods using polyhydric alcohols (JP-A-58-180,233 and JP-A-61-16,903), methods using polyglycidyl compounds, polyaziridine compounds, polyamine compounds, and polyisocyanate compounds (JP-A-59-189,103), a method which uses glyoxal (JP-A-52-117, 393), methods using polyvalent metals (JP-A-51-136,588, JP-A-61-257,235, and JP-A-62-7,745), methods using silane coupling agents (JP-A-61-211,305, JP-61-252,212, and JP-A-61-264,006), a method using an epoxy compound and a hydroxy compound (JP-A-02-132,103), and a method using an alkylene carbonate (DE-4020780) respectively as cross-linking agents have been known. Further, methods requiring the presence of inert inorganic powders (JP-A-60-163,956 and JP-A-60-255,814), a method requiring the presence of a dihydric alcohol (JP-A-01-292,004), a method requiring the presence of water and an ether compound (JP-A-02-153,903), and a method requiring the presence of the alkylene oxide adduct of a monohydric alcohol, an organic acid salt, and lactam (EP No. 555692) respectively during the course of the cross-linking treatment have been known to the art.

These methods accomplish the balanced improvement of the physical properties of the absorbent resin and the exaltation of the amount of an aqueous liquid to be absorbed by the absorbent resin under load to a certain extent. When the liquid to be absorbed happens to be blood, however, the amount of blood to be absorbed by the absorbent resin is unduly small because the components of the blood envelope the individual absorbent resin particles during the absorption of blood to interfere the absorption. Particularly for use in such articles as sanitary napkins, the absorbent resins known heretofore do not necessarily produce satisfactory results. For the purpose of improving the capacity of the absorbent resin for absorbing blood, it has been proposed to add such compounds as sodium chloride and polyethylene glycol to the absorbent resin (JP-A-58-501,107 and JP-A-54-70,694). Though the mutual adhesion of the particles of the absorbent resin is indeed prevented in this case, the effect actually attained falls short of the expectation because the absorbent resin absorbs blood at an unduly low speed in an insufficient amount.

An attempt to improve the blood absorption ratio of a sanitary material grade non-woven fabric by rendering ununiform the highly absorbent fibers in the fabric of highly absorbent fibers (JP-A-06-207,358) and attempts to improve the speed of absorption and the wet back of artificial menstrual blood with a laminate using absorbent resins differing in particle size in an upper and a lower layer thereof (JP-U-06-59,039), an absorbent material formed of an absorbent resin, an inorganic powder, and a polyhydric alcohol (JP-U-06-58,952), and a laminate combining the laminate and the absorbent material mentioned above (JP-U-06-58, 931) have been proposed. Though these constructions indeed improve the ratio of blood absorption, the speed of absorption, and the wet back to a certain extent, the effects actually attained thereby fall short of the expectation because the absorbent resins used therein absorb blood at low speeds and the suction power thereof is insufficient.

The absorbent resins heretofore known to the art are not fully satisfactory because their absorption characteristics manifested to aqueous liquids and particularly to blood are not sufficient. An object of this invention, therefore, is to provide a novel blood-absorbable resin composition resulting from improving the absorbing power of an absorbent resin relative to blood and an absorbent article containing the composition. The blood-absorbable resin composition of this invention is applicable advantageously for such products as sanitary napkins, tampons, medical blood-absorbable articles, trauma protectors, trauma healing materials, and reagents for treating liquid refuses from surgical operations.

DISCLOSURE OF INVENTION

The present inventors continued a diligent study regarding absorbent resins with a view to fulfilling the object mentioned above. They have consequently found that an absorbent resin possessing a specific blood area ratio manifests excellent absorption characteristics to blood. The present invention has been perfected as a result.

Specifically, this invention concerns a blood-absorbable resin composition characterized by having a blood area ratio relative to sheep blood of not less than 30% at a basis weight of 150 g/m$^2$.

This invention further concerns the blood-absorbable resin composition characterized by being obtained by mixing the absorbent resin with a surface-cross-linking agent, granulating the resultant mixture, and subsequently heat-treating the granulated mixture.

This invention further concerns the blood-absorbable resin, wherein the surface-cross-linking agent is a polyhydric alcohol or an alkylene carbonate.

This invention further concerns the blood-absorbable resin, wherein the heat treatment is carried out under the conditions satisfying the following formula (1):

$$\log_e t \geq 15.7 \times 10^3 (1/T) - 24.4 \quad (1)$$

wherein t is the duration of heat treatment (in seconds) and T is the absolute temperature (K).

This invention further concerns the blood-absorbable resin, wherein the mixture proceeds between 100 parts by weight of the absorbent resin and 0.5 to 10 parts by weight of the surface-cross-linking agent.

This invention further concerns the blood-absorbable resin, wherein the absorbent resin has an average particle size in the range of 20 to 100 μm.

This invention further concerns the blood-absorbable resin, wherein the granulation is effected in the form of extrusion granulation.

This invention further concerns the blood-absorbable resin, wherein the extrusion granulation is carried out by the use of an extrusion type granulating device provided with a spherical perforated plate containing holes of a diameter in the range of 0.3 to 0.8 mm.

This invention further concerns the blood-absorbable resin, wherein the blood surface area is not less than 20% at a basis weight of 2400 g/m².

This invention further concerns the blood-absorbable resin, wherein the blood surface area is not less than 10% at a basis weight of 9600 g/m².

This invention further concerns an absorbent article containing the blood-absorbable resin composition mentioned above.

BEST MODE FOR CARRYING OUT THE INVENTION

Now, this invention will be described more specifically below.

The blood-absorbable resin composition of this invention is a novel resin composition excelling in absorption characteristics relative to blood and characterized by having a blood area ratio of not less than 30% at a basis weight of 150 g/m² relative to sheep blood. The term "blood area ratio" as used herein is a characteristic value significantly correlated with the absorption characteristics of an absorbent resin relative to blood and is determined by a method which will be described hereinbelow. Absorbent resins which are capable of sucking artificial urine in large amounts have been known to the art. These known absorbent resins are deficient in such absorption characteristics as the amounts of blood to be sucked because their blood area ratios do not reach the minimum level specified by this invention. Incidentally, it has been found that the blood area ratio mentioned above is extremely important for such products as sanitary napkins which contain an absorbent resin composition at a high ratio (the content of the absorbent resin in the absorbent structure is 50% by weight or more). The blood-absorbable resin composition which has a blood area ratio relative to sheep blood of not less than 30% at a basis weight of 150 g/m² manifests high suction power and retaining power to blood. When this blood-absorbable resin composition is applied for such absorbent articles as sanitary napkins, it quickly absorbs the blood which has been diffused in the hydrophilic fibrous material carrying the blood-absorbable resin composition and stably retains the diffusing property of the hydrophilic fibrous material in spite of the effect of aging. It, therefore, permits manufacture of absorbent articles which inflict no unpleasant sensation on the skin and incur wet back of blood only sparingly.

The blood area ratio to be manifested by the blood-absorbable resin composition of this invention to sheep blood is not less than 30%, preferably not less than 50%, at a basis weight of 150 g/m². If the blood area ratio is less than 30% at a basis weight of 150 g/m², the amount of blood sucked by the blood-absorbable resin composition will be unduly small and the properties, particularly the amount of wet back, to be manifested by an absorbent article which is produced with the blood-absorbable resin composition will be inferior. For the purpose of further increasing the amount of blood to be sucked by the blood-absorbable resin composition, it is appropriate that the blood area ratio mentioned above be not less than 20%, preferably not less than 30%, at a basis weight of 2400 g/m² and further that the blood area ratio be not less than 10%, preferably not less than 15%, at a basis weight of 9600 g/m².

Now, one example of the method for the production of the blood-absorbable resin composition of this invention will be cited below. The blood-absorbable resin composition of this invention is not particularly discriminated on account of the method of its production so long as the blood area ratio thereof satisfies the requirement specified by this invention.

The blood-absorbable resin composition of this invention can be produced by mixing an absorbent resin with a surface-cross-linking agent, extrusion granulating the resultant mixture by the use of an extrusion type granulating device thereby forming absorbent resin granules, and subsequently heat-treating the granules.

The absorbent resin mentioned above has no particular restriction except for the requirement that it be capable of absorbing water and consequently undergoing voluminal expansion. Generally, it is obtained by polymerizing a water-soluble unsaturated monomer. As typical examples of the water-soluble unsaturated monomer, anionic monomers such as (meth)acrylic acid, maleic acid (anhydride), fumaric acid, crotonic acid, itaconic acid, 2-(meth)acryloylethane sulfonic acid, 2-(meth)acroylpropane sulfonic acid, 2-(meth)acrylamide-2-methyl propane sulfonic acid, vinyl sulfonic acid, and styrene sulfonic acid and salts thereof; nonionic hydrophilic group-containing monomers such as (meth)acrylamide, N-substituted (meth)acrylamides, 2-hydroxyethyl (meth)acrylates, 2-hydroxypropyl (meth) acrylates, methoxypolyethylene glycol (meth)acrylates, and polyethylene glycol (meth)acrylates; and amino group-containing unsaturated monomers such as N,N-dimethylaminoethyl (meth)acrylates, N,N-dimethylaminopropyl (meth) acrylates, and N,N-dimethylaminopropyl (meth)acrylamide and quaternary compounds thereof may be cited. The water-soluble unsaturated monomer may incorporate therein such a hydrophobic monomer as is selected from among acrylic esters including methyl (meth)acrylate, ethyl (meth)acrylate, and butyl (meth)acrylate, vinyl acetate, and vinyl propionate in such an amount as is incapable of noticeably inhibiting the hydrophilicity of the produced polymer. These monomer components may be used either singly or in the form of a combination of two or more members. In consideration of the absorption characteristics of the finally obtained absorbent article, however, it is advantageous to use at least one member selected from the group consisting of (meth)acrylic acid (salts), 2-(meth)acryloylethane sulfonic acids (salts), 2-(meth)acrylamide-2-methyl propane sulfonic acids (salts), (meth)acrylamides, methoxy polyethylene glycol (meth) acrylates, N,N-dimethylaminoethyl (meth)acrylate, and quaternary products thereof. It is more proper for the monomer component to contain therein a (meth)acrylic acid (salt) as an essential component. Most properly in this case, the (meth)acrylic acid has a proportion, 30 to 90 mol %, thereof neutralized with a basic substance. Properly, the absorbent resin has a ratio of absorption capacity with absorbed water in the approximate range of 20 to 60 g/g, as determined by the tea bag method carried out in physiological saline solution. Properly, the proportion of the non-cross-linked component, namely the so-called water-soluble component, is not more than 20% by weight.

More properly, this proportion is not more than 10% by weight. The less the proportion, the better.

The absorbent resin mentioned above may be of the self-cross-linking type obtained without using a cross-linking agent or of the type obtained by using a cross-linking agent containing a polymerizable unsaturated group and/or a reactive functional group to such an extent that the properties of the produced absorbent resin will reach the prescribed levels. As typical examples of the inner cross-linking agent to be used for cross-linking the interior of the absorbent resin in this case, N,N'-methylene bis(meth)acrylamide, (poly)ethylene glycol (meth)acrylates, glycerol tri(meth)acrylate, trimethylolpropane tri(meth)acrylate, triallyl amine, triallyl cyanurate, triallyl isocyanurate, glycidyl (meth)acrylates, (poly)ethyleneglycol, diethyleneglycol, (poly)glycerol, propylene glycol, diethanol amine, trimethylol propane, pentaerythritol, (poly)ethylene glycol diglycidyl diether, (poly)glycerol polyglycidyl ether, epichlorohydrin, ethylene diamine, polyethylene imine, (poly)aluminum chloride, aluminum sulfate, calcium chloride, and magnesium sulfate may be cited. These inner cross-linking agents may be used either singly or in the form of a combination of two or more members in consideration of the reactivity.

In the production of the absorbent resin mentioned above, the formation of a graft linkage or complex may be simultaneously attained with the polymerization by polymerizing the monomer component mentioned above in the presence of a hydrophilic polymeric compound such as starch, cellulose, or polyvinyl alcohol.

As typical examples of the polymerization initiator to be used in the polymerization of the monomer component mentioned above, such water-soluble radical polymerization initiators such as ammonium persulfate, potassium persulfate, sodium persulfate, hydrogen peroxide, t-butyl hydroperoxide, and 2,2'-azobis-amidinopropane dihydrochloride may be cited. The method for effecting this polymerization has no restriction in any way. For example, bulk polymerization, aqueous solution polymerization, and reversed-phase suspension polymerization are available for the polymerization under discussion.

The absorbent resins enumerated above maybe used either singly or in the form of a mixture of two or more members.

The absorbent resin particles mentioned above are not particularly discriminated on account of the shape thereof. They may be in the form of flakes obtained by drying the particles in a drum or in the form of amorphous grains obtained by pulverizing lumps of resin. Alternatively, they may be in the form of spheres obtained by the reversed-phase suspension polymerization.

Though the average particle size of the absorbent resin mentioned above is not particularly defined, it is appropriately in the range of 10 to 400 μm. It is particularly proper to be in the range of 20 to 100 μm in consideration of the blood absorption properties of the blood-absorbable resin composition to be obtained. If the average particle size of the absorbent resin deviates from the range mentioned above, the disadvantage follows that the blood area ratio of the produced blood-absorbable resin composition will tend to decrease.

The surface-cross-linking agent mentioned above is intended to cross-link the neighborhood of surface of the absorbent resin. It has no particular restriction except for the requirement that it possesses two or more functional groups capable of reacting with the functional group in the surface of the absorbent resin and exhibits safety when used in such an absorbent article as a sanitary napkin. As typical examples of the surface-cross-linking agent that answers the description, polyhydric alcohols such as ethylene glycol, diethylene glycol, triethylene glycol, polyethylene glycol, propylene glycol, polypropylene glycol, trimethylene glycol, 1,3-propanediol, 1,4-butanediol, 1,5-pentanediol, 1,6-hexanediol, 1,7-heptanediol, 1,8-octanediol, 1,9-nonanediol, pinacol, hydrobenzoin, benzpinacol, cyclopentane-1,2-diol, cyclohexane-1,4-diol, pentaerythritol, glycerol, diglycerol, polyglycerol, diethanolamine, triethanolamine, polyoxypropylene, oxyethyleneoxypropylene block polymer, sorbitol, sorbitan, sorbitan fatty acid esters, polyoxyethylene sorbitan fatty acid esters, trimethylolpropane, pentaerythritol, polyvinyl alcohol, glucose, mannit, mannitan, sucrose, and glucose; alkylene carbonates such as ethylene carbonate, propylene carbonate, 4,5-dimethyl-1,4-dioxoran-2-on, 4,4-dimethyl-1,3-dioxoran-2-on, 4-ethyl-1,3-dioxoran-2-on, 4-hydroxymethyl-1,3-dioxoran-2-on, 1,3-dioxan-2-on, 4-methyl-1,3-dioxan-2-on, and 4,6-dimethyl-1,3-dioxan-2-on; polyamines such as ethylenediamine, diethylenetriamine, triethylenetetramine, tetraethylenepentamine, pentaethylenehexamine, and polyethyleneimine; polyisocyanates such as 2,4-tolylene diisocyanate and hexamethylene diisocyanate; polyoxazoline such as 1,2-ethylene bisoxazoline; and polyaziridines such as 2,2-bishydroxymethyl butanol-tris-[3-(1-aziridyl)propionate], 1,6-hexamethylene diethylene urea, and diphenyl methane-bis-4,4'-N,N'-diethylene urea may be cited. The surface-cross-linking agents may be used either singly or in the form of a mixture of two or more members. Among other surface-cross-linking agents enumerated above, ethylene glycol, diethylene glycol, triethylene glycol, polyethylene glycol, propylene glycol, glycerol, diglycerol, polyglycerol, ethylene carbonate, and propylene carbonate prove particularly preferable and glycerol proves most preferable from the viewpoint of the blood area ratio relative to sheep blood of the produced blood-absorbable resin composition.

Though the amount of the surface-cross-linking agent to be used is not particularly defined, it is appropriate in the range of 0.5 to 10 parts by weight, preferably in the range of 2 to 5 parts by weight, based on 100 parts by weight of the absorbent resin. If the amount mentioned above is less than 0.5 part by weight, even an elongation of the heating time will not easily bring about a discernible increase in the blood area ratio of the produced blood-absorbable resin composition. Conversely, if this amount exceeds 10 parts by weight, the excess will not only fail to produce any easy proportionate addition to the effect aimed at but also survive as an unaltered substance and consequently cause various troubles and impair the economy of the operation.

For the purpose of uniformizing and ensuring the mixture of the absorbent resin and the surface-cross-linking agent, it is permissible to use 0 to 50 parts by weight of water and 0 to 60 parts by weight of a hydrophilic organic solvent, based on 100 parts by weight of the absorbent resin. As typical examples of the water, distilled water, deionized water, and tap water may be cited. The hydrophilic organic solvent is required to be capable of being uniformly mixed with the surface-cross-linking agent and avoiding to exert an adverse effect on the performance of the absorbent resin. As typical examples of the hydrophilic organic solvent that answers this description, lower alcohols such as methanol, ethanol, n-propanol, isopropanol, n-butanol, isobutanol, sec-butanol, and t-butanol; ketones such as acetone, methylethyl ketone, and methyl isobutyl ketone, ethers such as dioxane, tetrahydrofuran, and diethyl ether; amides such as N,N-dimethyl formamide and N,N-diethyl formamide; and sulfoxides such as dimethyl sulfoxide may be cited.

The production of the blood-absorbable resin composition of this invention is initiated by mixing the absorbent resin mentioned above with the surface-cross-linking agent mentioned above. The method for effecting this mixture is not particularly defined. An ordinary mixing device can be used. The mixing device that is advantageously used for mixing the absorbent resin mentioned above with the surface-cross-linking agent mentioned above has no particular restriction except for the requirement that it be capable of uniformly mixing them. As typical examples of the mixing device that answers the description, cylindrical mixing device, double-wall conical mixing device, V-shaped mixing device, ribbon type mixing device, screw type mixing device, fluidized bed type mixing device, rotary disc type mixing device, gas stream type mixing device, twin arm type kneading device, inner mixing device, crusher type kneading device, rotary mixing device, and screw type extruding device may be cited.

After the absorbent resin mentioned above and the surface-cross-linking agent mentioned above have been mixed, the mixture consequently obtained is granulated. Though the method for effecting this granulation is not particularly defined, it is proper to use the method of extrusion granulation. Any of the heretofore known methods of extrusion granulation can be adopted. The method of extrusion granulation comprises producing granules by the use of a device which is provided with an extruding part and a die or screen and adapted to convert a given material into granules of a fixed size by means of extrusion. As typical examples of the device that answers this description, screw frontal extrusion type granulating device, screw lateral extrusion type granulating device, screw vacuum extrusion type granulating device, screw combination pretreating and extrusion granulating device, roll ring die type extrusion granulating device, blade basket type extrusion granulating device, blade oscillating type extrusion granulating device, self-molding gear type extrusion granulating device, and self-molding cylinder type extrusion granulating device may be cited. In consideration of the convenience of operation and the productivity, it is preferable to adopt the screw frontal extrusion type granulating device and more preferable to use the extrusion granulating device that is provided with a spherical perforated plate having a spherical die or screen. The shape of the holes perforated in the die or screen of the extrusion granulating device provided with the spherical perforated plate is not particularly defined. It may be arbitrarily selected from among true circles, ellipses, polygons such as hexagons, and triangles, for example, to suit the purpose for which the produced granules are to be used. The hole diameter (in the case of holes of the shape of true circle) is not particularly restricted. When the produced granules are to be used for a sanitary article, for example, the hole diameter is properly in the range of 0.1 to 1.0 mm, preferably 0.3 to 0.8 mm. If the hole diameter is less than 0.1 mm, the extrusion of the material through the holes will not be easily effected with high efficiency and the sanitary article formed with the produced granules will suffer from poor permeability to liquid because of the unduly small particle size. Conversely, if the hole diameter exceeds 1.0 mm, the produced granules of blood-absorbable resin composition will be unduly large and, consequently, will possibly require to undergo an extra work of disintegration or pulverization.

The absorbent resin granules which are aimed at are obtained by subjecting the absorbent resin mixture comprising the absorbent resin mentioned above and the surface-cross-linking agent mentioned above to the treatment with such an extrusion granulating device as mentioned above. For the purpose of further uniformizing the particle size distribution of the produced granules, the granules of the absorbent resin which are discharged from the extrusion granulating device maybe subjected to a treatment for the adjustment of particle size.

For the purpose of minimizing the occurrence of unduly minute particles in the granules, the treatment for particle size adjustment is advantageously carried out by continuously subjecting the granules freshly discharged from the granulating device to the action of a particle size-uniformizing device, namely by treating the granules with this device while the granules keep a highly plastic state. Though the particle size-uniformizing device thus used is not particularly discriminated on account of its kind, it is proper to adopt such a type of particle size-uniformizing device that is provided within a cylindrical housing thereof with a ratable particle size-uniformizing disc set in place coaxially relative to the rotary housing and further provided with a multiplicity of nozzles communicating with an external air feeding mechanism and opening into local parts of the cylindrical housing and functioning to form a rotary current of air jet inside the housing by spouting air through the plurality of nozzles into the housing. In this particle size-uniformizing device, the granulated particles (absorbent resin granules) that is supplied through a hopper disposed above the cylindrical housing into the housing is uniformly diffused inside the housing by a dispersing disc disposed above the particle size-uniformizing disc mentioned above and kept in rotation and is then subjected to the particle size-uniformizing owing to the rotating action produced by the particle size-uniformizing disc in rotation and the crushing and regulating action produced by the jet air spouted through the nozzles. The particle size-uniformizing device constructed as described above has an additional effect of preventing the granules freshly discharged from the extrusion granulating device from mutual adhesion because the jet air is capable of expelling the surface-cross-linking agent adhering to the surface of the granules.

Then, the absorbent resin granules obtained as described above is given a heat treatment. When the surface-cross-linking agent mentioned above happens to be a polyhydric alcohol or an alkylene carbonate, the heat treatment is advantageously carried out on the condition that the temperature of the granules and the duration of the heating satisfy the following formula (1).

$$log_e t \geq 15.7 \times 10^3 (1/T) - 24.4 \qquad (1)$$

wherein t is the duration of heat treatment (in seconds) and T is the absolute temperature (K).

If the heat treatment is carried out under the condition that does not satisfy this formula, the produced blood-absorbable resin composition will be deficient in the blood area ratio. The condition under which the heat treatment is performed preferably satisfies the following formula (2).

$$15.7 \times 10^3 (1/T) - 23 \geq log_e t \geq 15.7 \times 10^3 (1/T) - 24.4 \qquad (2)$$

wherein t is the duration of heat treatment (in seconds) and T is the absolute temperature (K).

If the heat treatment is carried out under the condition that does not satisfy the left expression of the formula (2), the extra time to be inevitably spent will not easily bring about a proportionate addition to the expected effect and impair the economy of the heat treatment.

This condition of heat treatment is different from that which has been heretofore held at appropriate. The blood area ratio that has never been attained to date can be accomplished when the heat treatment is performed under the specific condition of heat treatment represented by the formula mentioned above.

When the surface-cross-linking agent is a polyhydric alcohol or an alkylene carbonate, the specific temperature of the granules under treatment and the specific duration of the heat treatment are properly not less than 18 hours and not more than 70 hours at 170° C. through not less than 5 minutes and not more than 18 minutes at 250° C., preferably not less than 8 hours and not more than 30 hours at 180° C. through not less than 1 hour and not more than 3 hours at 210° C. If the temperature of the granules under treatment is less than 170° C., the time required for producing the blood-absorbable resin composition having a high blood area ratio is so much as to impair the economy of the heat treatment. If the temperature of the granules under treatment conversely exceeds 250° C., the excess heat will possibly induce thermal degradation of the granules, depending on the kind of absorbent resin to be used.

The method to be used for the heat treatment of the present invention is not critical. Any of the standard drying devices and heating furnaces such as, for example, groove type stirring and drying devices, rotary drying devices, fluidized-bed drying devices, gas stream drying devices, infrared drying devices, and induction heating devices can be used for the heat treatment. For the purpose of allowing the produced blood-absorbable resin composition to acquire as high a blood area ratio as possible, it is proper to adopt a device which generates as low shear force or crushing force as permissible. Among the devices enumerated above, therefore, the fluidized-bed drying device and the gas stream drying device prove particularly advantageous.

The blood-absorbable resin composition of this invention is not particularly discriminated on account of its size. With consideration for the absorption characteristics of the absorbent article to be ultimately obtained, the average particle size of the blood-absorbable resin composition is appropriately in the range of 100 to 1000 $\mu$m, preferably in the range of 200 to 600 $\mu$m. If the average particle size of the blood-absorbable resin composition is less than 100 $\mu$m, the absorbent article to be ultimately obtained will tend to manifest inferior permeability to liquid. If the average particle size exceeds 1000 $\mu$m, the produced blood-absorbable resin composition will tend to manifest an unduly low speed of absorption and the absorbent article will possibly inflict a physically objectionable sensation on the user thereof.

As a hydrophilic fibrous substance useful for the absorbent article of this invention, it is appropriate to use an air-laid pad of fluff wood pulp. The construction of this air-laid pad is well known in the field of the production of disposable diapers disclosed in U.S. Pat. No. 4,610,678, for example. As typical examples of the hydrophilic fibrous substance to be used effectively in this invention, cotton linters, cross-linked cellulose fibers disclosed in EP No. 429112 and No. 427316, rayon, cotton, wool, acetate, and vinylon besides the ground pump mentioned above may be cited.

The absorbent article of this invention is composed of the blood-absorbable resin composition mentioned above and hydrophilic fibers. These components of the article are caused to form a matrix in a mutually mixed state or in a state dispersed on a fibrous sheet. The formation of the absorbent article may be attained in several manners including the method currently adopted for the manufacture of disposable diapers available in the market. Appropriate methods which are available for the formation of the absorbent article are disclosed in U.S. Pat. No. 4,578,068, No. 4,666,975, No. 4,673,402, No.4,765,780, No. 5,047,023, and No. 5,156,902, for example. The absorbent article which is obtained as described above is compression molded to a density in the range of 0.06 to 0.5 g/cc and a basis weight in the range of 0.01 to 0.20 g/cm$^2$.

The absorbent article of this invention obtained by the combination of the blood-absorbable resin composition mentioned above with the hydrophilic fibers, for the purpose of acquiring an improved ability to retain its shape after absorbing water, is allowed to have thermoplastic fibers incorporated in the hydrophilic fibers thereof. As typical examples of the thermoplastic fibers which are used effectively for the incorporation, polyethylene, polypropylene, and polyester fibers, and polyester, polyamide, and binary fiber copolymers, and also compound fibers thereof may be cited.

The absorbent article of this invention may be further provided with numerous component members such as diffused layer, elastic member for the leg, elastic member for the waist, and tape which are well known in the pertinent technical field.

The absorbent article of this invention is applicable for various products such as sanitary napkins, tampons, medical blood-absorbable articles, trauma protectors, trauma healing materials, and reagents for treating liquid refuses from surgical operations which require to absorb large volumes of blood.

The blood-absorbable resin composition or the absorbent article obtained by this invention, when necessary, may be vested with new functions by incorporating therein such additives as deodorant, perfume, inorganic powder, foaming agent, pigment, dye, hydrophilic filaments, fertilizer, oxidizing agent, reducing agent, water, and salts.

Now, this invention will be described more specifically below with reference to working examples. It should be noted, however, that this invention is not limited to these examples.

The average particle size, the blood area ratio relative to sheep blood, and the suction power of sheep blood which are referred to concerning the absorbent resin or the blood-absorbable resin composition and the wet back of sheep blood which is referred to concerning the absorbent article in the following referential examples, working examples, and controls represent the relevant magnitudes determined by the following methods.

(1) Average Particle Size

This property was determined by classifying a sample resin with JIS (Japanese Industrial Standard) standard sieves (20 mesh, 32 mesh, 48 mesh, 60 mesh, 100 mesh, 145 mesh, 200 mesh, and 350 mesh), plotting residual percentage ratios R on a logarithmic probability chart, finding the particle size corresponding to R=50%, and reporting the found particle size.

(2) Blood Area Ratio Relative to Sheep Blood

This property was determined by placing a metal net (10 mesh) measuring 80 mm and 90 mm in area at the center of a cylindrical container measuring 150 mm in inside diameter and 65 mm in height, injecting about 50 g of sheep blood (sheep defibrinated blood; produced by Nippon Bio-Test Laboratories Inc.), uniformly scattering a sample resin in a prescribed basis weight in a cylindrical cell measuring 60 mm in inside diameter and 50 mm in height and having a metal net (400 mesh) spread on the bottom, causing the cell to stand at rest for 5 minutes on the metal net in the cylindrical container, then photographing the cell from above with a camera, analyzing the photograph with an image analyzing and processing device (LA-1000; produced by PIAS Co., Ltd.), measuring the areas in which the sample resin had sucked blood and the total area of the sample resin, and calculating the blood area ratio defined by the following formula.

Blood area ratio (%) =
[(Areas in which the sample resin sucked blood)/
(Total area of sample resin)] × 100

(3) Suction Power of Sheep Blood

This property was determined by placing 1 g of a sample resin on a pile of 16 sheets of toilet paper (55 mm×75 mm) immersed in 20 ml of sheep blood held in a petri dish, 95 mm in inside diameter, allowing the sample resin to absorb the sheep blood for 5 minutes, then collecting a swelled gel consequently formed, weighing the swelled gel, and calculating the suction power of sheep blood by the sample resin (g/g) by dividing the weight of the swelled gel by the original weight of the sample resin.

(4) Wet Back of Sheep Blood

This property was determined by dropping about 25 g of sheep blood with a syringe onto the central part of a given absorbent article, allowing the sheep blood to stand on the absorbent article for about 5 minutes, and rating wet back by touching the surface of the absorbent article with a hand.

REFERENTIAL EXAMPLE 1

In a jacketed twin arm type kneader of stainless steel, 10 liters in inner volume, provided with two sigma type vanes, 4400 g of an aqueous solution of a monomer component comprising 75 mol % of sodium acrylate and 25 mol % of acrylic acid (monomer component concentration 37% by weight) and 2.72 g of trimethylolpropane triacrylate (0.05 mol % based on the monomer component) as a cross-linking agent were placed and nitrogen gas was blown in to displace the interior of the reaction system with nitrogen. Then, the two sigma type vanes were set rotating and the interior of the reaction system was heated by passing hot water at 30° C. through the jacket while adding 1.10 g of sodium persulfate as an initiator and 1.10 g of sodium sulfite to the reaction system. The aqueous monomer solution, with the advance of polymerization, formed a soft hydrated gel and underwent gradual division by the rotation of the vanes. After 40 minutes of the polymerization, the produced polymer gel was dried with hot air on a metal net at a temperature of 150° C. for two hours and the dried polymer gel was crushed with a hammer mill. The resultant powder was classified with a metal net of 60 mesh to obtain a referential absorbent resin (1) having an average particle size of 123 µm.

REFERENTIAL EXAMPLE 2

The powder obtained in Referential Example 1 was classified with a metal net of 90 mesh to obtain a referential absorbent resin (2) having an average particle size of 84 µm.

REFERENTIAL EXAMPLE 3

The powder obtained in Referential Example 1 was classified with a metal net of 145 mesh to obtain a referential absorbent resin (3) having an average particle size of 50 µm.

REFERENTIAL EXAMPLE 4

The polymerization of an absorbent resin was performed by following the procedure of Referential Example 1 while placing 4400 g of an aqueous solution of a monomer consisting of 75 mol % of sodium acrylate and 25 mol % of acrylic acid (monomer component concentration 37% by weight) and 1.36 g of trimethylolpropane triacrylate (0.025 mol % based on monomer component) instead. A referential absorbent resin (4) having an average particle size of 84 µm was obtained by classifying the produced powder with a metal net of 90 mesh.

REFERENTIAL EXAMPLE 5

A referential absorbent resin (5) was obtained by pulverizing the referential absorbent resin (4) obtained in Referential Example 4 by the use of a high-speed jet pulverizing device (Model LJ, produced by Nippon Pneumatic MFG. Co., Ltd. and marketed under trademark designation of "Labojet") until it acquired an average particle size of 34 µm.

REFERENTIAL EXAMPLE 6

A referential absorbent resin (6) was obtained by pulverizing the referential absorbent resin (1) obtained in Referential Example 1 by the use of a high-speed jet pulverizing device until it acquired an average particle size of 24 µm.

REFERENTIAL EXAMPLE 7

A referential absorbent resin (7) was obtained by pulverizing the referential absorbent resin (1) obtained in Referential Example 1 by the use of a high-speed jet pulverizing device until it acquired an average particle size of 15 µm.

REFERENTIAL EXAMPLE 8

A referential absorbent resin (8) having an average particle size of 250 µm was obtained by classifying the powder obtained in Referential Example 1 with a metal net of 40 mesh.

REFERENTIAL EXAMPLE 9

A referential absorbent resin (9) having an average particle size of 350 µm was obtained by classifying the powder obtained in Referential Example 1 with a metal net of 20 mesh.

REFERENTIAL EXAMPLE 10

The polymerization of an absorbent resin was performed by following the procedure of Referential Example 1 while placing 4400 g of an aqueous solution of a monomer comprising 70 mol % of sodium acrylate and 30 mol % of acrylic acid (monomer component concentration 37% by weight) and 2.76 g of trimethylolpropane triacrylate (0.05 mol % based on monomer component) instead. A referential absorbent resin (10) having an average particle size of 250 µm was obtained by classifying the produced powder with a metal net of 40 mesh.

REFERENTIAL EXAMPLE 11

The polymerization of an absorbent resin was performed by following the procedure of Referential Example 1 while placing 4400 g of an aqueous solution of a monomer comprising 65 mol % of sodium acrylate and 35 mol % of acrylic acid (monomer component concentration 37% by weight) and 2.79 g of trimethylolpropane triacrylate (0.05 mol % based on monomer component) instead. A referential absorbent resin (11) having an average particle size of 250 µm was obtained by classifying the produced powder with a metal net of 40 mesh.

REFERENTIAL EXAMPLE 12

The polymerization of an absorbent resin was performed by following the procedure of Referential Example 1 while placing 4400 g of an aqueous solution of a monomer comprising 60 mol % of sodium acrylate and 40 mol % of acrylic acid (monomer component concentration 37% by weight) and 2.83 g of trimethylolpropane triacrylate (0.05 mol % based on monomer component) instead. A referential absorbent resin (12) having an average particle size of 250 µm was obtained by classifying the produced powder with a metal net of 40 mesh.

REFERENTIAL EXAMPLE 13

The polymerization of an absorbent resin was performed by following the procedure of Referential Example 1 while placing 4400 g of an aqueous solution of a monomer comprising 50 mol % of sodium acrylate and 50 mol % of acrylic acid (monomer component concentration 37% by weight) and 2.90 g of trimethylolpropane triacrylate (0.05 mol % based on monomer component) instead. A referential absorbent resin (13) having an average particle size of 250 µm was obtained by classifying the produced powder with a metal net of 40 mesh.

REFERENTIAL EXAMPLE 14

A referential absorbent resin (14) having an average particle size of 250 µm was obtained by classifying the powder obtained in Referential Example 4 with a metal net of 40 mesh.

REFERENTIAL EXAMPLE 15

The polymerization of an absorbent resin was performed by following the procedure of Referential Example 1 while placing 4400 g of an aqueous solution of a monomer comprising 50 mol % of sodium acrylate and 50 mol % of acrylic acid (monomer component concentration 37% by weight) and 1.45 g of trimethylolpropane triacrylate (0.025 mol % based on monomer component) instead. A referential absorbent resin (15) having an average particle size of 250 µm was obtained by classifying the produced powder with a metal net of 40 mesh.

EXAMPLE 1

One hundred (100) parts by weight of the referential absorbent resin (2) obtained in Referential Example 2 and 2.5 parts by weight of glycerol were mixed by the use of a mixer (produced by Lödige Corp. and marketed under trademark designation of "Lödige M5R") for about 30 minutes. The produced absorbent resin mixture was extrusion granulated by the use of a screw type frontal extrusion type granulating device, holes of 0.4 mm in diameter, (produced by Fuji Paudal Co., Ltd. and marketed under trademark designation of Dome Gran DG-L1") provided with a spherical die. The produced absorbent resin granules consequently obtained was treated by the use of a wet type continuous particle size-uniformizing device (produced by Fuji Paudal Co., Ltd. and marketed under trademark designation of "Turbo-Comminuter") to obtain a blood-absorbable resin composition (1) having an average particle size of 350 am.

EXAMPLE 2

A blood-absorbable resin composition (2) having an average particle size of 330 µm was obtained by following the procedure of Example 1 while using 100 parts by weight of the referential absorbent resin (3) obtained in Referential Example 3 and 2.5 parts by weight of diglycerol instead.

EXAMPLE 3

A blood-absorbable resin composition (3) having an average particle size of 300 µm was obtained by following the procedure of Example 1 while using 100 parts by weight of the referential absorbent resin (4) obtained in Referential Example 4 and 3.5 parts by weight of glycerol instead.

EXAMPLE 4

A blood-absorbable resin composition (4) having an average particle size of 450 µm was obtained by following the procedure of Example 1 while using 100 parts by weight of the referential absorbent resin (6) obtained in Referential Example 5 and 2.5 parts by weight of polyglycerol and changing the die hole diameter of the granulating device to 0.6 mm instead.

EXAMPLE 5

A blood-absorbable resin composition (5) having an average particle size of 390 µm was obtained by following the procedure of Example 1 while using 100 parts by weight of the referential absorbent resin (2) obtained in Referential Example 2 and 5 parts by weight of glycerol and performing the heat treatment at 210° C. for one hour instead.

EXAMPLE 6

A blood-absorbable resin composition (6) having an average particle size of 160 µm was obtained by following the procedure of Example 1 while using 100 parts by weight of the referential absorbent resin (7) obtained in Referential Example 7 and 2.5 parts by weight of glycerol instead.

EXAMPLE 7

A blood-absorbable resin composition (7) having an average particle size of 390 µm was obtained by following the procedure of Example 1 while using 100 parts by weight of the referential absorbent resin (1) obtained in Referential Example 1 and 2.5 parts by weight of glycerol instead.

EXAMPLE 8

A blood-absorbable resin composition (8) having an average particle size of 310 µm was obtained by following the procedure of Example 1 while using 100 parts by weight of the referential absorbent resin (2) obtained in Referential Example 2 and 1 part by weight of glycerol instead.

EXAMPLE 9

A blood-absorbable resin composition (9) having an average particle size of 390 µm was obtained by following the procedure of Example 1 while using 100 parts by weight of the referential absorbent resin (1) obtained in Referential Example 1 and 8 parts by weight of glycerol instead.

EXAMPLE 10

A blood-absorbable resin composition (10) having an average particle size of 840 µm was obtained by following the procedure of Example 1 while changing the die hole diameter of the granulating device to 1.2 mm.

EXAMPLE 11

A blood-absorbable resin composition (11) was obtained by mixing an aqueous solution containing 100 parts by weight of the referential absorbent resin (2) obtained in Referential Example 2, 0.5 part by weight of glycerol, 2 parts by weight of water, and 0.5 part by weight of isopropanol by the use of a Lödige mixer for about 30 minutes, placing the resultant absorbent resin mixture in a drying device, and heating the resin mixture therein at 220° C. for two hours.

EXAMPLE 12

A blood-absorbable resin composition (12) was obtained by following the procedure of Example 11 while using an aqueous solution containing 100 parts by weight of the referential absorbent resin (2) obtained in Referential Example 2, 1 part by weight of diglycerol, 4 parts by weight of water, and 1 part by weight of isopropanol and performing the heat treatment at 220° C. for one hour instead.

EXAMPLE 13

A blood-absorbable resin composition (13) was obtained by following the procedure of Example 11 while using an aqueous solution containing 100 parts by weight of the referential absorbent resin (2) obtained in Referential Example 2, 1 part by weight of propylene glycol, 4 parts by weight of water, and 1 part by weight of isopropanol and performing the heat treatment at 240° C. for 20 minutes instead.

EXAMPLE 14

A blood-absorbable resin composition (14) was obtained by following the procedure of Example 11 while using an aqueous solution containing 100 parts by weight of the referential absorbent resin (2) obtained in Referential Example 2, 1 part by weight of ethylene carbonate, 4 parts by weight of water, and 1 part by weight of isopropanol and performing the heat treatment at 240° C. for one hour instead.

EXAMPLE 15

A blood-absorbable resin composition (15) was obtained by following the procedure of Example 11 while using 100 parts by weight of the referential absorbent resin (2) obtained in Referential Example 2 and 2.5 parts by weight of glycerol and performing the heat treatment at 240° C. for two hours instead.

EXAMPLE 16

A blood-absorbable resin composition (16) was obtained by following the procedure of Example 11 while using 100 parts by weight of the referential absorbent resin (2) obtained in Referential Example 2 and 2.5 parts by weight of glycerol and performing the heat treatment at 200° C. for two hours instead.

EXAMPLE 17

A blood-absorbable resin composition (17) was obtained by following the procedure of Example 11 while using 100 parts by weight of the referential absorbent resin (2) obtained in Referential Example 2 and 2.5 parts by weight of glycerol and performing the heat treatment at 180° C. for 10 hours instead.

EXAMPLE 18

A blood-absorbable resin composition (18) was obtained by following the procedure of Example 11 while using an aqueous solution containing 100 parts by weight of the referential absorbent resin (9) obtained in Referential Example 9, 1 part by weight of glycerol, 4 parts by weight of water, and 1 part by weight of isopropanol instead.

EXAMPLE 19

A blood-absorbable resin composition (19) was obtained by following the procedure of Example 11 while using an aqueous solution containing 100 parts by weight of the referential absorbent resin (9) obtained in Referential Example 9, 1 part by weight of propylene glycol, 4 parts by weight of water, and 1 part by weight of isopropanol and performing the heat treatment at 240° C. for one hour instead.

EXAMPLE 20

A blood-absorbable resin composition (20) was obtained by following the procedure of Example 11 while using an aqueous solution containing 100 parts by weight of the referential absorbent resin (8) obtained in Referential Example 8, 1 part by weight of ethylene carbonate, 4 parts by weight of water, and 1 part by weight of isopropanol and performing the heat treatment at 200° C. for two hours instead.

EXAMPLE 21

A blood-absorbable resin composition (21) was obtained by following the procedure of Example 11 while using an aqueous solution containing 100 parts by weight of the referential absorbent resin (10) obtained in Referential Example 10, 1 part by weight of glycerol, 4 parts by weight of water, and 1 part by weight of isopropanol and performing the heat treatment at 200° C. for two hours instead.

EXAMPLE 22

A blood-absorbable resin composition (22) was obtained by following the procedure of Example 11 while using an aqueous solution containing 100 parts by weight of the referential absorbent resin (11) obtained in Referential Example 11, 1 part by weight of glycerol, 4 parts by weight of water, and 1 part by weight of isopropanol and performing the heat treatment at 200° C. for two hours instead.

EXAMPLE 23

A blood-absorbable resin composition (23) was obtained by following the procedure of Example 11 while using an aqueous solution containing 100 parts by weight of the referential absorbent resin (12) obtained in Referential Example 12, 1 part by weight of glycerol, 4 parts by weight of water, and 1 part by weight of isopropanol and performing the heat treatment at 200° C. for two hours instead.

EXAMPLE 24

A blood-absorbable resin composition (24) was obtained by following the procedure of Example 11 while using an aqueous solution containing 100 parts by weight of the referential absorbent resin (13) obtained in Referential Example 13, 1 part by weight of glycerol, 4 parts by weight of water, and 1 part by weight of isopropanol and performing the heat treatment at 200° C. for two hours instead.

EXAMPLE 25

A blood-absorbable resin composition (25) was obtained by following the procedure of Example 11 while using an aqueous solution containing 100 parts by weight of the referential absorbent resin (14) obtained in Referential Example 14, 1 part by weight of ethylene carbonate, 4 parts by weight of water, and 1 part by weight of isopropanol and performing the heat treatment at 220° C. for one hour instead.

EXAMPLE 26

A blood-absorbable resin composition (26) was obtained by following the procedure of Example 11 while using an aqueous solution containing 100 parts by weight of the referential absorbent resin (14) obtained in Referential Example 14, 1 part by weight of glycerol, 4 parts by weight of water, and 1 part by weight of isopropanol and performing the heat treatment at 200° C. for two hours instead.

EXAMPLE 27

A blood-absorbable resin composition (27) was obtained by following the procedure of Example 11 while using an aqueous solution containing 100 parts by weight of the referential absorbent resin (14) obtained in Referential Example 14, 1 part by weight of glycerol, 4 parts by weight of water, and 1 part by weight of isopropanol and performing the heat treatment at 180° C. for 10 hours instead.

EXAMPLE 28

A blood-absorbable resin composition (28) was obtained by following the procedure of Example 11 while using an aqueous solution containing 100 parts by weight of the referential absorbent resin (15) obtained in Referential Example 15, 1 part by weight of ethylene carbonate, 4 parts by weight of water, and 1 part by weight of isopropanol and performing the heat treatment at 200° C. for 2 hours instead.

Control 1

An absorbent resin (1) for comparison having an average particle size of 100 μm was obtained by following the procedure of Example 1 while omitting the use of glycerol.

Control 2

An absorbent resin (2) for comparison having an average particle size of 290 μm was obtained by following the procedure of Example 1 while performing the heat treatment at 200° C. for 30 minutes instead.

Control 3

An absorbent resin (3) for comparison having an average particle size of 280 μm was obtained by following the procedure of Example 1 while performing the heat treatment at 210° C. for 20 minutes instead.

Control 4

An absorbent resin (4) for comparison was obtained by mixing 100 parts by weight of the referential absorbent resin (2) obtained in Referential Example 2 with 2.5 parts by weight of glycerol by the use of a Lödige mixer for about 30 minutes.

Control 5

An absorbent resin (5) for comparison having an average particle size of 320 μm was obtained by following the procedure of Example 1 while performing the heat treatment at 200° C. for one hour instead.

Control 6

An absorbent resin (6) for comparison was obtained by mixing 67 parts by weight of the referential absorbent resin (2) obtained in Referential Example 2 with 33 parts by weight of potassium chloride.

Control 7

An absorbent resin (7) for comparison was obtained by mixing 100 parts by weight of the referential absorbent resin (2) obtained in Referential Example 2 with 5 parts by weight of polyethylene glycol having a molecular weight of 300.

Control 8

An absorbent resin (8) for comparison was obtained by mixing 100 parts by weight of the referential absorbent resin (2) obtained in Referential Example 2 with 3 parts by weight of glycerol and 1 part by weight of hydrophilic silicon dioxide (produced by Nippon Aerosil Co., Ltd. and marketed under trademark designation of "Aerosil 200").

Control 9

An absorbent resin (9) for comparison was obtained by following the procedure of Example 11 while performing the heat treatment at 180° C. for one hour.

Control 10

An absorbent resin (10) for comparison was obtained by following the procedure of Example 11 while using an aqueous solution containing 100 parts by weight of the referential absorbent resin (2) obtained in Referential Example 2, 1 part by weight of diglycerin, 4 parts by weight of water, and 1 part by weight of isopropanol and performing the heat treatment at 180° C. for two hours instead.

Control 11

An absorbent resin (11) for comparison was obtained by following the procedure of Example 11 while using an aqueous solution containing 100 parts by weight of the referential absorbent resin (2) obtained in Referential Example 2, 1 part by weight of propylene glycol, 4 parts by weight of water, and 1 part by weight of isopropanol and performing the heat treatment at 200° C. for 20 minutes instead.

Control 12

An absorbent resin (12) for comparison was obtained by following the procedure of Example 11 while using an aqueous solution containing 100 parts by weight of the referential absorbent resin (2) obtained in Referential Example 2, 1 part by weight of ethylene carbonate, 4 parts by weight of water, and 1 part by weight of isopropanol and performing the heat treatment at 200° C. for one hour instead.

Control 13

An absorbent resin (13) for comparison was obtained by following the procedure of Example 11 while using 100 parts by weight of the referential absorbent resin (2) obtained in Referential Example 2 and 2.5 parts by weight of glycerol and performing the heat treatment at 220° C. for 20 minutes instead.

Control 14

An absorbent resin (14) for comparison was obtained by following the procedure of Example 11 while using 100 parts by weight of the referential absorbent resin (14) obtained in Referential Example 14 and 2.5 parts by weight of glycerol and performing the heat treatment at 180° C. for two hours instead.

Control 15

An absorbent resin (15) for comparison was obtained by following the procedure of Example 11 while using 100 parts by weight of the referential absorbent resin (14) obtained in Referential Example 14 and 2.5 parts by weight of glycerol and performing the heat treatment at 200° C. for 20 minutes instead.

Control 16

An absorbent resin (16) for comparison was obtained by following the procedure of Example 11 while using an aqueous solution containing 100 parts by weight of the referential absorbent resin (14) obtained in Referential Example 14, 1 part by weight of propylene glycol, 4 parts by weight of water, and 1 part by weight of isopropanol and performing the heat treatment at 200° C. for one hour instead.

Control 17

An absorbent resin (17) for comparison was obtained by following the procedure of Example 11 while using an aqueous solution containing 100 parts by weight of the referential absorbent resin (14) obtained in Referential Example 14, 1 part by weight of ethylene carbonate, 4 parts by weight of water, and 1 part by weight of isopropanol and performing the heat treatment at 220° C. for 20 minutes instead.

EXAMPLE 29

A blood-absorbable resin structure having a density of 0.15 g/cc and a basis weight of 0.05 g/cm$^2$ was obtained by dry mixing 100 parts by weight of the blood-absorbable resin composition (1) obtained in Example 1 with 100 parts by weight of fluff pulp, pneumatically spreading the resultant mixture in the form of a sheet, and compressing the sheet. Then, an absorbent article (1) composed of a section, 6 cm×20 cm, (about 12 g in weight) cut from the absorbent resin structure mentioned above, a top sheet made of polypropylene permeable to liquid, two sheets of tissue paper, a liquid-impermeable polyethylene back sheet containing a leg gather and a waist gather, and two tape fasteners was manually assembled by tying the component layers with a double-faced adhesive tape. The total weight of the absorbent article (1) was about 23 g.

EXAMPLES 30 TO 37 AND CONTROLS 18 to 26

Blood-absorbable resin structures of this invention and absorbent resin structures for comparison having a density in the approximate range of 0.13 to 0.17 g/cc and a basis weight in the range of 0.047 to 0.053 g/cm$^2$ were obtained by following the procedure of Example 29 while using the blood-absorbable resin compositions (4), (11), (13), (14), (18), (25), (27) or (28) or the absorbent resin compositions for comparison (1), (2), (4), (6), (9), (11), (12), (15), or (17) in place of the blood-absorbable resin (1). Absorbent articles (2) to (9) of this invention and absorbent articles for comparison (1) to (9) were produced by following the procedure of Example 29 while using the blood-absorbable resin structures of this invention or the absorbent resin structures for comparison instead.

The properties of the blood-absorbable resin compositions (1) to (28) obtained in Examples 1 to 28 are shown in Table 1, the properties of the resin compositions for comparison (1) to (15) obtained in Referential Examples 1 to 15 are shown in Table 2, the properties of the absorbent resins for comparison (1) to (17) obtained in Controls 1 to 17 are shown in Table 3, and the properties of the absorbent articles (1) to (9) of this invention obtained in Examples 29 to 37 and the absorbent articles for comparison (1) to (9) obtained in Controls 18 to 26 are shown in Table 4.

TABLE 1

| | Suction power of sheep blood (g/g) | Blood area ratio relative to sheep blood (%) | | |
|---|---|---|---|---|
| | | Basis weight 150 g/m$^2$ | Basis weight 2400 g/m$^2$ | Basis weight 9600 g/m$^2$ |
| Example 1 (Blood-absorbable resin composition 1) | 14.2 | 99 | 98 | 96 |
| Example 2 (Blood-absorbable resin composition 2) | 14.1 | 98 | 98 | 97 |
| Example 3 (Blood-absorbable resin composition 3) | 13.9 | 99 | 100 | 98 |
| Example 4 (Blood-absorbable resin composition 4) | 14.2 | 100 | 99 | 97 |
| Example 5 (Blood-absorbable resin composition 5) | 14.3 | 97 | 97 | 96 |
| Example 6 (Blood-absorbable resin composition 6) | 7.1 | 74 | 4 | 2 |
| Example 7 (Blood-absorbable resin composition 7) | 8.9 | 82 | 21 | 1 |
| Example 8 (Blood-absorbable resin composition 8) | 9.4 | 81 | 17 | 4 |
| Example 9 (Blood-absorbable resin composition 9) | 8.3 | 69 | 18 | 3 |
| Example 10 (Blood-absorbable resin composition 10) | 7.9 | 72 | 24 | 3 |
| Example 11 (Blood-absorbable resin composition 11) | 12.4 | 95 | 94 | 94 |
| Example 12 (Blood-absorbable resin composition 12) | 10.2 | 96 | 95 | 11 |
| Example 13 (Blood-absorbable resin composition 13) | 10.0 | 97 | 95 | 13 |
| Example 14 (Blood-absorbable resin composition 14) | 12.2 | 99 | 98 | 94 |
| Example 15 (Blood-absorbable resin composition 15) | 12.4 | 98 | 97 | 95 |
| Example 16 (Blood-absorbable resin composition 16) | 9.4 | 78 | 20 | 3 |

TABLE 1-continued

|  | Suction power of sheep blood (g/g) | Blood area ratio relative to sheep blood (%) | | |
|---|---|---|---|---|
|  |  | Basis weight 150 g/m$^2$ | Basis weight 2400 g/m$^2$ | Basis weight 9600 g/m$^2$ |
| Example 17 (Blood-absorbable resin composition 17) | 8.7 | 81 | 20 | 5 |
| Example 18 (Blood-absorbable resin composition 18) | 12.0 | 99 | 97 | 93 |
| Example 19 (Blood-absorbable resin composition 19) | 11.9 | 99 | 98 | 92 |
| Example 20 (Blood-absorbable resin composition 20) | 8.2 | 65 | 15 | 4 |
| Example 21 (Blood-absorbable resin composition 21) | 9.4 | 78 | 22 | 3 |
| Example 22 (Blood-absorbable resin composition 22) | 10.3 | 98 | 97 | 17 |
| Example 23 (Blood-absorbable resin composition 23) | 11.7 | 99 | 98 | 91 |
| Example 24 (Blood-absorbable resin composition 24) | 12.3 | 96 | 97 | 94 |
| Example 25 (Blood-absorbable resin composition 25) | 9.2 | 84 | 24 | 2 |
| Example 26 (Blood-absorbable resin composition 26) | 8.1 | 72 | 12 | 2 |
| Example 27 (Blood-absorbable resin composition 27) | 5.9 | 56 | 4 | 3 |
| Example 28 (Blood-absorbable resin composition 28) | 10.0 | 98 | 96 | 15 |

TABLE 2

|  | Suction power of sheep blood (g/g) | Blood area ratio relative to sheep blood (%) | | |
|---|---|---|---|---|
|  |  | Basis weight 150 g/m$^2$ | Basis weight 2400 g/m$^2$ | Basis weight 9600 g/m$^2$ |
| Referential Example 1 (Absorbent resin 1 for reference) | 1.2 | 3 | 2 | 1 |
| Referential Example 2 (Absorbent resin 2 for reference) | 1.3 | 2 | 6 | 0 |
| Referential Example 3 (Absorbent resin 3 for reference) | 1.5 | 3 | 3 | 2 |
| Referential Example 4 (Absorbent resin 4 for reference) | 1.2 | 4 | 7 | 0 |
| Referential Example 5 (Absorbent resin 5 for reference) | 1.4 | 2 | 4 | 0 |
| Referential Example 6 (Absorbent resin 6 for reference) | 1.1 | 5 | 3 | 4 |
| Referential Example 7 (Absorbent resin 7 for reference) | 1.2 | 6 | 4 | 0 |
| Referential Example 8 (Absorbent resin 8 for reference) | 1.5 | 2 | 1 | 2 |
| Referential Example 9 (Absorbent resin 9 for reference) | 1.8 | 3 | 8 | 5 |
| Referential Example 10 (Absorbent resin 10 for reference) | 1.4 | 1 | 5 | 8 |
| Referential Example 11 (Absorbent resin 11 for reference) | 2.0 | 4 | 3 | 3 |
| Referential Example 12 (Absorbent resin 12 for reference) | 1.9 | 2 | 4 | 4 |
| Referential Example 13 (Absorbent resin 13 for reference) | 2.1 | 5 | 5 | 8 |
| Referential Example 14 (Absorbent resin 14 for reference) | 1.4 | 6 | 3 | 7 |
| Referential Example 15 (Absorbent resin 15 for reference) | 1.6 | 7 | 3 | 3 |

TABLE 3

|  | Suction power of sheep blood (g/g) | Blood area ratio relative to sheep blood (%) | | |
| --- | --- | --- | --- | --- |
|  |  | Basis weight 150 g/m$^2$ | Basis weight 2400 g/m$^2$ | Basis weight 9600 g/m$^2$ |
| Control 1 (Absorbent resin 1 for comparison) | 2.4 | 12 | 4 | 2 |
| Control 2 (Absorbent resin 2 for comparison) | 3.6 | 24 | 8 | 1 |
| Control 3 (Absorbent resin 3 for comparison) | 3.5 | 19 | 5 | 0 |
| Control 4 (Absorbent resin 4 for comparison) | 2.8 | 9 | 7 | 1 |
| Control 5 (Absorbent resin 5 for comparison) | 3.8 | 22 | 4 | 2 |
| Control 6 (Absorbent resin 6 for comparison) | 2.7 | 14 | 3 | 1 |
| Control 7 (Absorbent resin 7 for comparison) | 2.0 | 4 | 2 | 0 |
| Control 8 (Absorbent resin 8 for comparison) | 2.4 | 3 | 2 | 0 |
| Control 9 (Absorbent resin 9 for comparison) | 2.6 | 13 | 1 | 0 |
| Control 10 (Absorbent resin 10 for comparison) | 3.6 | 22 | 6 | 3 |
| Control 11 (Absorbent resin 11 for comparison) | 3.0 | 14 | 2 | 0 |
| Control 12 (Absorbent resin 12 for comparison) | 3.7 | 19 | 5 | 2 |
| Control 13 (Absorbent resin 13 for comparison) | 3.9 | 21 | 5 | 1 |
| Control 14 (Absorbent resin 14 for comparison) | 3.9 | 17 | 7 | 2 |
| Control 15 (Absorbent resin 15 for comparison) | 2.5 | 13 | 4 | 1 |
| Control 16 (Absorbent resin 16 for comparison) | 3.6 | 17 | 3 | 2 |
| Control 17 (Absorbent resin 17 for comparison) | 3.8 | 16 | 4 | 1 |

TABLE 4

|  | Wet back of sheep blood |
| --- | --- |
| Example 29 (Absorbent article of this invention 1) | ⊚ |
| Example 30 (Absorbent article of this invention 2) | ⊚ |
| Example 31 (Absorbent article of this invention 3) | ⊚ |
| Example 32 (Absorbent article of this invention 4) | ⊚ |
| Example 33 (Absorbent article of this invention 5) | ⊚ |
| Example 34 (Absorbent article of this invention 6) | ⊚ |
| Example 35 (Absorbent article of this invention 7) | ○ |
| Example 36 (Absorbent article of this invention 8) | ○ |
| Example 37 (Absorbent article of this invention 9) | ⊚ |
| Control 18 (Absorbent article for comparison 1) | xx |
| Control 19 (Absorbent article for comparison 2) | x |
| Control 20 (Absorbent article for comparison 3) | xx |
| Control 21 (Absorbent article for comparison 4) | xx |
| Control 22 (Absorbent article for comparison 5) | xx |
| Control 23 (Absorbent article for comparison 6) | xx |
| Control 24 (Absorbent article for comparison 7) | x |
| Control 25 (Absorbent article for comparison 8) | xx |
| Control 26 (Absorbent article for comparison 9) | x |

⊚ . . . Pleasing and excellent dry sensation
○ . . . Dry sensation free from tackiness
x . . . Slight tackiness and no dry sensation
xx . . . Glutinousness and no dry sensation

INDUSTRIAL APPLICABILITY

The blood-absorbable resin composition of this invention possesses an excellent ability to absorb blood and, therefore, is highly useful for sanitary napkins, tampons, medical blood-absorbable articles, trauma protectors, trauma healing materials, and reagents for treating liquid refuses from surgical operations.

We claim:

1. A blood-absorbable resin composition comprising a blood area ratio relative to sheep blood of not less than 30% at a basis weight of 150 g/m$^2$.

2. The blood-absorbable resin composition according to claim 1, wherein said composition is obtained by mixing an absorbent resin with a surface-cross-linking agent, granulating the resultant mixture, and subjecting the produced granules to a heat treatment.

3. The blood-absorbable resin composition according to claim 2, wherein said surface-cross-linking agent is a polyhydric alcohol or an alkylene carbonate.

4. The blood-absorbable resin composition according to claim 2, wherein said heat treatment is carried out under the conditions satisfying the following formula (1)

$$\log_e t \geq 15.7 \times 10^3 (1/T) - 24.4 \tag{1}$$

wherein t is the duration of heat treatment (in seconds) and T is the absolute temperature (K).

5. The blood-absorbable resin composition according to claim 2, wherein said mixing is effected between 100 parts by weight of said absorbent resin and 0.5 to 10 parts by weight of said surface-cross-linking agent.

6. The blood-absorbable resin composition according to claim 2, wherein said absorbent resin has an average particle size in the range of 20 to 100 μm.

7. The blood-absorbable resin composition according to claim 2, wherein said granulation is effected in the form of extrusion granulation.

8. The blood-absorbable resin composition according to claim 7, wherein said extrusion granulation is carried out by the use of an extrusion type granulating device provided with a spherical perforated plate containing holes 0.3 to 0.8 mm in diameter.

9. The blood-absorbable resin composition according to claim 1, wherein said blood area ratio is not less than 20% at a basis weight of 2400 $g/m^2$.

10. The blood-absorbable resin composition according to claim 9, wherein said blood area ratio is not less than 10% at a basis weight of 9600 $g/m^2$.

11. The absorbent article containing said blood-absorbable resin composition set forth in claim 1.

* * * * *